(12) United States Patent
McCorkle et al.

(10) Patent No.: US 10,849,876 B2
(45) Date of Patent: *Dec. 1, 2020

(54) APPARATUSES, METHODS AND SYSTEMS FOR EXTRACTION, ISOLATION AND CONVERSION OF VARIOUS CANNABINOIDS, AND MODIFICATIONS OF WHOLE-PLANT HEMP EXTRACTS THEREWITH

(71) Applicant: Charlotte's Web, Inc., Boulder, CO (US)

(72) Inventors: Alexander Michael McCorkle, Coveland, CO (US); Graham Taylor Carlson, Boulder, CO (US); Shelby Renee Sheahan, Boulder, CO (US)

(73) Assignee: Charlotte's Web, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/853,199

(22) Filed: Apr. 20, 2020

(65) Prior Publication Data

US 2020/0261407 A1 Aug. 20, 2020

Related U.S. Application Data

(63) Continuation of application No. 16/023,732, filed on Jun. 29, 2018, now Pat. No. 10,624,872.

(60) Provisional application No. 62/526,875, filed on Jun. 29, 2017.

(51) Int. Cl.
| | | |
|---|---|---|
| A61K 36/00 | (2006.01) |
| A61K 31/352 | (2006.01) |
| A61K 36/185 | (2006.01) |
| C07C 37/70 | (2006.01) |
| A61K 31/047 | (2006.01) |
| A23L 33/105 | (2016.01) |
| C07D 311/80 | (2006.01) |

(52) U.S. Cl.
CPC .......... *A61K 31/352* (2013.01); *A23L 33/105* (2016.08); *A61K 31/047* (2013.01); *A61K 36/185* (2013.01); *C07C 37/70* (2013.01); *C07D 311/80* (2013.01); *A23V 2002/00* (2013.01)

(58) Field of Classification Search
CPC ...................................................... A61K 36/00
USPC ........................................................ 424/725
See application file for complete search history.

(56) References Cited

U.S. PATENT DOCUMENTS

| | | |
|---|---|---|
| 9,340,475 B2 | 5/2016 | Mona et al. |
| PP27,475 P2 | 12/2016 | Kubby |
| PP30,639 P2 | 7/2019 | Stanley |
| 10,351,498 B2 | 7/2019 | Mona et al. |
| 10,624,872 B1 | 4/2020 | McCorkle et al. |

OTHER PUBLICATIONS

Adams et al., "Structure of Cannabidiol. VI. Isomerization of Cannabidiol to Tetrahydrocannabinol, a Physiologically Active Product. Conversion of Cannabidiol to Cannabinol," 1940, 4 pages.
Ingold, "Desperate Journey: CBD in Colorado, Story 4, Pushing Ahead," The Denver Post Dec. 9, 2014, pp. 1-8. (Year: 2014).
Leinow & Birnbaum, foreword by Michael H. Moskowitz, MD., "CBD: A Patient's Guide to Medicinal Cannabis," sponsored by published by the Society for the Study of Native Arts and Sciences (dba North Atlantic Books) Chapter 8, (2017), 23 pages.
Pollastro et al., "Iodine-Promoted Aromatization of *p*-Menthane-Type Phytocannabinoids," J. Nat. Prod. 2018, 81, 630-633.
Quarles, Kentucky Department of Agriculture, "Industrial Hemp Research Pilot Program Summary of Varieties: Including Varieties of Concern and Prohibited Varieties," retrieved on Jul. 11, 2018, retrieved from the Internet at http://www.kyagr.com/marketing/documents/ HEMP_LH_Summary-of-Varieties.pdf, pp. 1-4, 2018. (Year: 2018).

*Primary Examiner* — Michael V Meller
(74) *Attorney, Agent, or Firm* — Cooley LLP

(57) ABSTRACT

Apparatuses, methods, and systems for extraction, isolation, purification, and conversion of various cannabinoids, and modifications of whole-plant hemp extracts therewith are presented. A method for preparing a whole-plant hemp extract based product includes extracting cannabinoids from plant materials, such as one or more hemp varieties of *Cannabis sativa*. The method also includes separating and purifying CBD from the extracted cannabinoids, converting purified CBD to Δ9-THC and Δ8-THC and concurrently converting Δ9-THC to CBN, purifying and separating the CBN, and combining the purified CBN with a whole-plan hemp extract. Products and supplements related to the method are also described.

18 Claims, 6 Drawing Sheets

APPARATUSES, METHODS AND SYSTEMS FOR EXTRACTION, ISOLATION AND CONVERSION OF VARIOUS CANNABINOIDS, AND MODIFICATIONS OF WHOLE-PLANT HEMP EXTRACTS THEREWITH

CROSS-REFERENCE TO RELATED APPLICATIONS

This application is a Continuation of U.S. patent application Ser. No. 16/023,732, filed Jun. 29, 2018 and entitled "APPARATUSES, METHODS AND SYSTEMS FOR EXTRACTION, ISOLATION AND CONVERSION OF VARIOUS CANNABINOIDS, AND MODIFICATIONS OF WHOLE-PLANT HEMP EXTRACTS THEREWITH," which issued as U.S. Pat. No. 10,624,872, on Apr. 21, 2020, which claims priority to and benefit of U.S. Provisional Patent Application No. 62/526,875, filed Jun. 29, 2017, the entire contents of which are incorporated herein by reference in their entireties.

FIELD

The present disclosure relates to plant-based compositions and methods of preparation thereof.

BACKGROUND

*Cannabis* is a flowering plant indigenous to central Asia and the Indian subcontinent, and grown worldwide. *Cannabis* is used industrially, medicinally, and recreationally.

SUMMARY

Various embodiments disclosed herein are generally directed to extraction, isolation, purification, and conversion of various cannabinoids, and modifications of whole-plant *Cannabis sativa* extracts therewith.

One embodiment of the present disclosure is directed to a method for preparing a whole-plant hemp extract based product, the method comprising: extracting cannabinoids from plant materials (such as one or more hemp varieties of *Cannabis sativa*), separating and purifying CBD from the extracted cannabinoids; converting purified CBD to Δ9-THC and Δ8-THC and concurrently converting Δ9-THC to CBN; purifying and separating the CBN; and combining the purified CBN with a whole-plant hemp extract. The method can include combining a carrier, such as a carrier oil and/or at least one further cannabinoid with the purified CBN and the whole-plant hemp extract, such as CBD, CBC, CBG, and/or CBDV.

Another embodiment of the present disclosure is directed to a product or supplement (such as a dietary supplement) formed by a method of the disclosure, including but not limited to the method(s) discussed above. In some embodiments, the product or supplement has a cannabinoid profile that is not found in nature. In some embodiments, the product or supplement has a CBD:Δ9-THC w:w ratio of 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 101:1, 102:1, 103:1, 104:1, 105:1, 106:1, 107:1, 108:1, 109:1, 110:1, 111:1, 112:1, 113:1, 114:1, 115:1, 116:1, 117:1, 118:1, 119:1, 120:1, 121:1, 122:1, 123:1, 124:1, 125:1, 126:1, 127:1, 128:1, 129:1, 130:1, 131:1, 132:1, 133:1, 134:1, 135:1, 136:1, 137:1, 138:1, 139:1, 140:1, 141:1, 142:1, 143:1, 144:1, 145:1, 146:1, 147:1, 148:1, 149:1, 150:1, 151:1, 152:1, 153:1, 154:1, 155:1, 156:1, 157:1, 158:1, 159:1, 160:1, 161:1, 162:1, 163:1, 164:1, 165:1, 166:1, 167:1, 168:1, 169:1, 170:1, 171:1, 172:1, 173:1, 174:1, 175:1, 176:1, 177:1, 178:1, 179:1, 180:1, 181:1, 182:1, 183:1, 184:1, 185:1, 186:1, 187:1, 188:1, 189:1, 190:1, 191:1, 192:1, 193:1, 194:1, 195:1, 196:1, 197:1, 198:1, 199:1, 200:1, 201:1, 202:1, 203:1, 204:1, 205:1, 206:1, 207:1, 208:1, 209:1, 210:1, 211:1, 212:1, 213:1, 214:1, 215:1, 216:1, 217:1, 218:1, 219:1, 220:1, 221:1, 222:1, 223:1, 224:1, 225:1, 226:1, 227:1, 228:1, 229:1, 230:1, 231:1, 232:1, 233:1, 234:1, 235:1, 236:1, 237:1, 238:1, 239:1, 240:1, 241:1, 242:1, 243:1, 244:1, 245:1, 246:1, 247:1, 248:1, 249:1, 250:1, 251:1, 252:1, 253:1, 254:1, 255:1, 256:1, 257:1, 258:1, 259:1, 260:1, 261:1, 262:1, 263:1, 264:1, 265:1, 266:1, 267:1, 268:1, 269:1, 270:1, 271:1, 272:1, 273:1, 274:1, 275:1, 276:1, 277:1, 278:1, 279:1, 280:1, 281:1, 282:1, 283:1, 284:1, 285:1, 286:1, 287:1, 288:1, 289:1, 290:1, 291:1, 292:1, 293:1, 294:1, 295:1, 296:1, 297:1, 298:1, 299:1, 300:1, 301:1, 302:1, 303:1, 304:1, 305:1, 306:1, 307:1, 308:1, 309:1, 310:1, 311:1, 312:1, 313:1, 314:1, 315:1, 316:1, 317:1, 318:1, 319:1, 320:1, 321:1, 322:1, 323:1, 324:1, 325:1, 326:1, 327:1, 328:1, 329:1, 330:1, 331:1, 332:1, 333:1, 334:1, 335:1, 336:1, 337:1, 338:1, 339:1, 340:1, 341:1, 342:1, 343:1, 344:1, 345:1, 346:1, 347:1, 348:1, 349:1, 350:1, 351:1, 352:1, 353:1, 354:1, 355:1, 356:1, 357:1, 358:1, 359:1, 360:1, 361:1, 362:1, 363:1, 364:1, 365:1, 366:1, 367:1, 368:1, 369:1, 370:1, 371:1, 372:1, 373:1, 374:1, 375:1, 376:1, 377:1, 378:1, 379:1, 380:1, 381:1, 382:1, 383:1, 384:1, 385:1, 386:1, 387:1, 388:1, 389:1, 390:1, 391:1, 392:1, 393:1, 394:1, 395:1, 396:1, 397:1, 398:1, 399:1, 400:1, 401:1, 402:1, 403:1, 404:1, 405:1, 406:1, 407:1, 408:1, 409:1, 410:1, 411:1, 412:1, 413:1, 414:1, 415:1, 416:1, 417:1, 418:1, 419:1, 420:1, 421:1, 422:1, 423:1, 424:1, 425:1, 426:1, 427:1, 428:1, 429:1, 430:1, 431:1, 432:1, 433:1, 434:1, 435:1, 436:1, 437:1, 438:1, 439:1, 440:1, 441:1, 442:1, 443:1, 444:1, 445:1, 446:1, 447:1, 448:1, 449:1, 450:1, 451:1, 452:1, 453:1, 454:1, 455:1, 456:1, 457:1, 458:1, 459:1, 460:1, 461:1, 462:1, 463:1, 464:1, 465:1, 466:1, 467:1, 468:1, 469:1, 470:1, 471:1, 472:1, 473:1, 474:1, 475:1, 476:1, 477:1, 478:1, 479:1, 480:1, 481:1, 482:1, 483:1, 484:1, 485:1, 486:1, 487:1, 488:1, 489:1, 490:1, 491:1, 492:1, 493:1, 494:1, 495:1, 496:1, 497:1, 498:1, 499:1, or 500:1.

In some embodiments, the product or supplement has a THC concentration less than 20% THC, less than 15% THC, less than 10% THC, less than 9.5% THC, less than 9% THC, less than 8.5% THC, less than 8% THC, less than 7.5% THC, less than 7% THC, less than 6.5% THC, less than 6% THC, less than 5.5% THC, less than 5% THC, less than 4.5% THC, less than 4% THC, less than 3.5% THC, less than 3% THC, less than 2.5% THC, less than 2% THC, less than 1.9% THC, less than 1.8% THC, less than 1.7% THC, less than 1.6% THC, less than 1.5% THC, less than 1.4% THC, less than 1.3% THC, less than 1.2% THC, less than 1.1% THC, less than 1% THC, less than 0.9% THC, less than 0.8% THC, less than 0.7% THC, less than 0.6% THC, less than 0.5% THC, less than 0.4% THC, less than 0.3% THC, less than 0.2% THC, less than 0.1% THC, less than 0.09% THC, less than 0.08% THC, less than 0.07% THC, less than 0.06% THC, less than 0.05% THC, less than 0.04% THC, less than 0.03% THC, less than 0.02% THC, or less than 0.01% THC, less than 0.009% THC, less than 0.008% THC, less than 0.007% THC, less than 0.006% THC, less than 0.005% THC, less than 0.004% THC, less than 0.003% THC, less than 0.002% THC, or less than 0.001% THC.

In some embodiments, the product or supplement includes a carrier oil. In some embodiments, the product or supplement has a CBN:CBD w:w ratio of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20.

The following publication(s) is/are hereby expressly incorporated herein by reference for all purposes:

Blessing, E. M., Steenkamp, M. M., Manzanares, J., & Marmar, C. R. (2015). Cannabidiol as a potential treatment for anxiety disorders. *Neurotherapeutics*, 12(4), 825-836.

Chong, Y., Fryer, C. D., & Gu, Q. (2013). Prescription sleep aid use among adults: United States, 2005-2010. *NCHS data brief*, (127), 1-8.

Crippa, J. A., Zuardi, A. W., Martin-Santos, R., Bhattacharyya, S., Atakan, Z., McGuire, P., & Fusar-Poli, P. (2009). Cannabis and anxiety: a critical review of the evidence. *Human Psychopharmacology: Clinical and Experimental*, 24(7), 515-523.

Cross, J. H., Devinsky, O., Marsh, E., Miller, I., Nabbout, R., Scheffer, I. E., & Wright, S. (2017). Cannabidiol (CBD) reduces convulsive seizure frequency in Dravet syndrome: results of a multi-center, randomized, controlled trial (GWPCARE1)(CT. 001). *Neurology*, 88(16 Supplement), CT-001.

Karniol, I. G., Shirakawa, I., Takahashi, R. N., Knobel, E., & Musty, R. E. (1975). Effects of Δ9-tetrahydrocannabinol and cannabinol in man. *Pharmacology*, 13(6), 502-512.

Pertwee, R. G. (2008). The diverse CB1 and CB2 receptor pharmacology of three plant cannabinoids: Δ9-tetrahydrocannabinol, cannabidiol and Δ9-tetrahydrocannabivarin. *British journal of pharmacology*, 153(2), 199-215.

Russo, E. B. (2011). Taming THC: potential *cannabis* synergy and phytocannabinoid-terpenoid entourage effects. *British journal of pharmacology*, 163(7), 1344-1364.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the disclosed subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Following below are detailed descriptions of various concepts related to, and embodiments of, the disclosed apparatuses, methods, and systems for extraction, isolation, purification, and conversion of various cannabinoids, and modifications of whole-plant *Cannabis sativa* extracts therewith. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

This disclosure relates to the purification of compounds extracted from hemp varieties of the *Cannabis sativa* plant and use thereof in dietary supplements, as well as dietary supplements comprising purified, converted compounds and whole-plant extracts. Hemp varieties of the *Cannabis sativa* plant typically have lower concentrations of tetrahydrocannabinol (THC) and higher concentrations of cannabidiol (CBD). Non-psychotropic and mildly psychotropic cannabinoids can be purified from material extracted from the whole plant. In addition, this disclosure details conversion of cannabidiol (CBD), the cannabinoid most abundant in hemp cultivars, into cannabinol (CBN).

Cannabinol (CBN) is a mildly psychotropic cannabinoid naturally found in the *Cannabis sativa* plant. It is a relatively weak CB1 and CB2 receptor agonist, with an order of magnitude less affinity than $(-)$-trans-$\Delta^9$-Tetrahydrocannabinol ($\Delta^9$-THC) (Pertwee 2008). It has been suggested anecdotally, and in at least one clinical study (Karniol et al. 1975), that CBN causes increased drowsiness in comparison to $(-)$-trans-$\Delta^9$-Tetrahydrocannabinol (Δ9-TI-IC). According to CDC, "4% of US adults aged 20 and over used prescription sleep aids in the past month" (Chong et al. 2013). Many prescription sleep aids carry inherent risk, including dependence in many cases. Thus, a market exists for naturally-derived sleep aids.

CBD has been demonstrated to reduce seizures in patients with Dravet syndrome (Cross et al, 2017), and additionally has an anxiolytic effect in humans (Blessing 2015). However, Δ9-THC is a potent CB1 agonist and as a result is psychotropic. It also has the common effect of increasing anxiety (Crippa et al. 2009). Even in hemp cultivars (<0.3% THC w/w) with high CBD, ratios of CBD to Δ9-THC are not commonly higher than 30:1. This results in significant doses of Δ9-THC as CBD doses are increased. In addition, it limits the amount of CBD that can be present in a hemp product.

Figure 1:
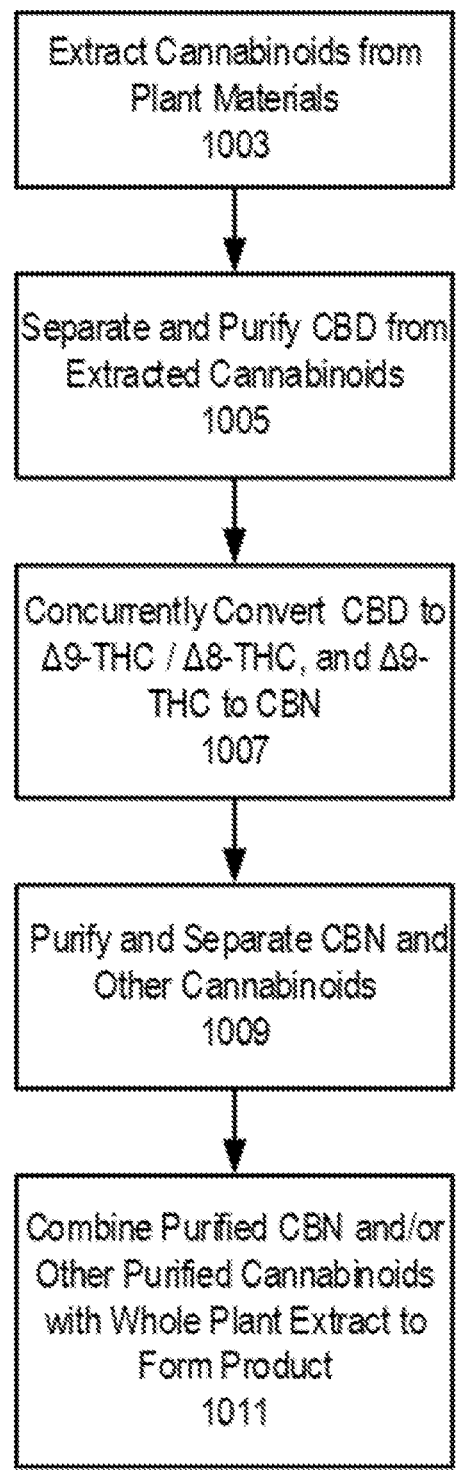
FIG. 1 is a flow diagram for a process/method of the disclosure.
Figure 2A:
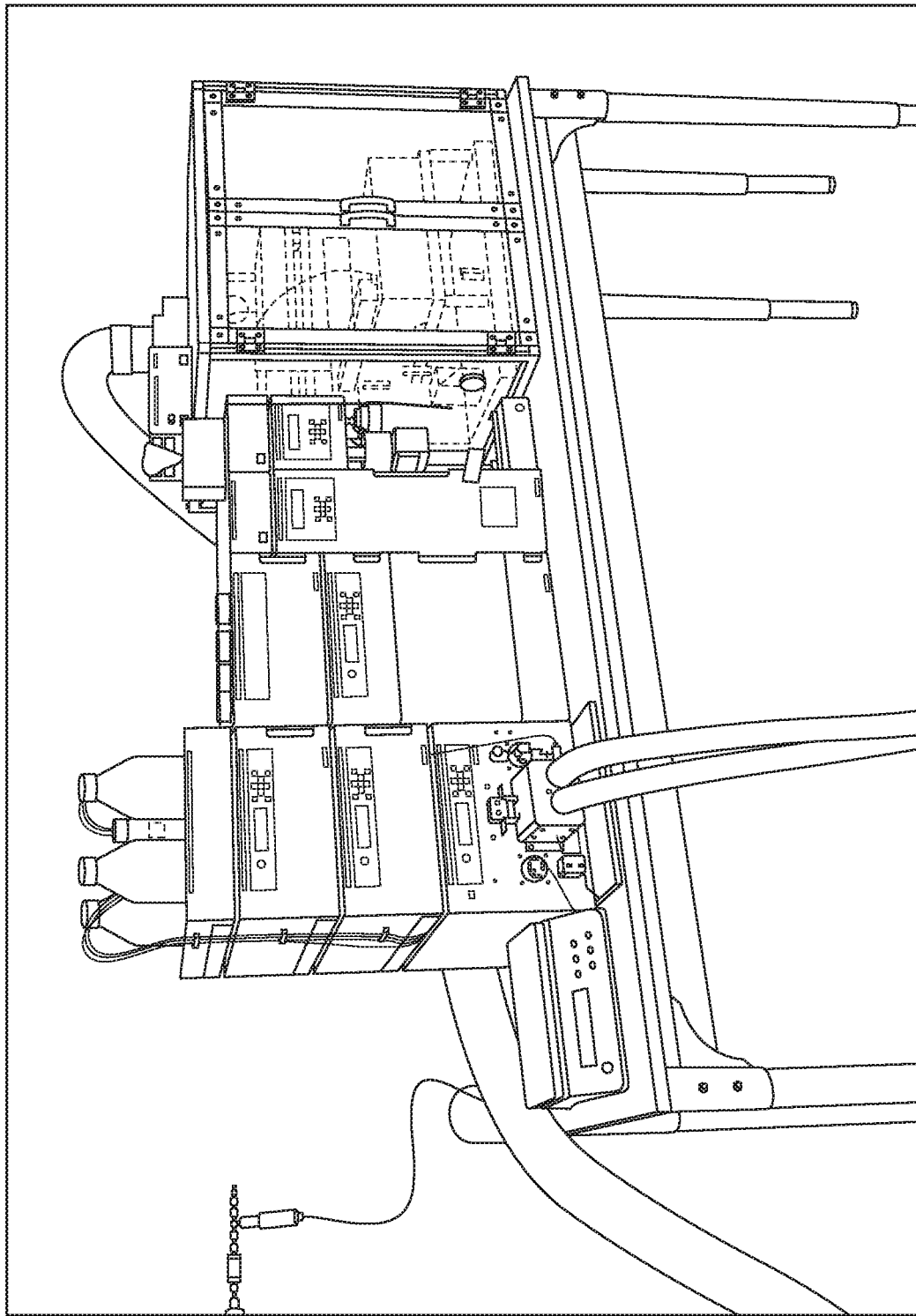
FIGS. 2A-2D illustrate example tools, equipment, and setups, including reactor and SFC setup, according to some embodiments of the disclosure.
Figure 2B:
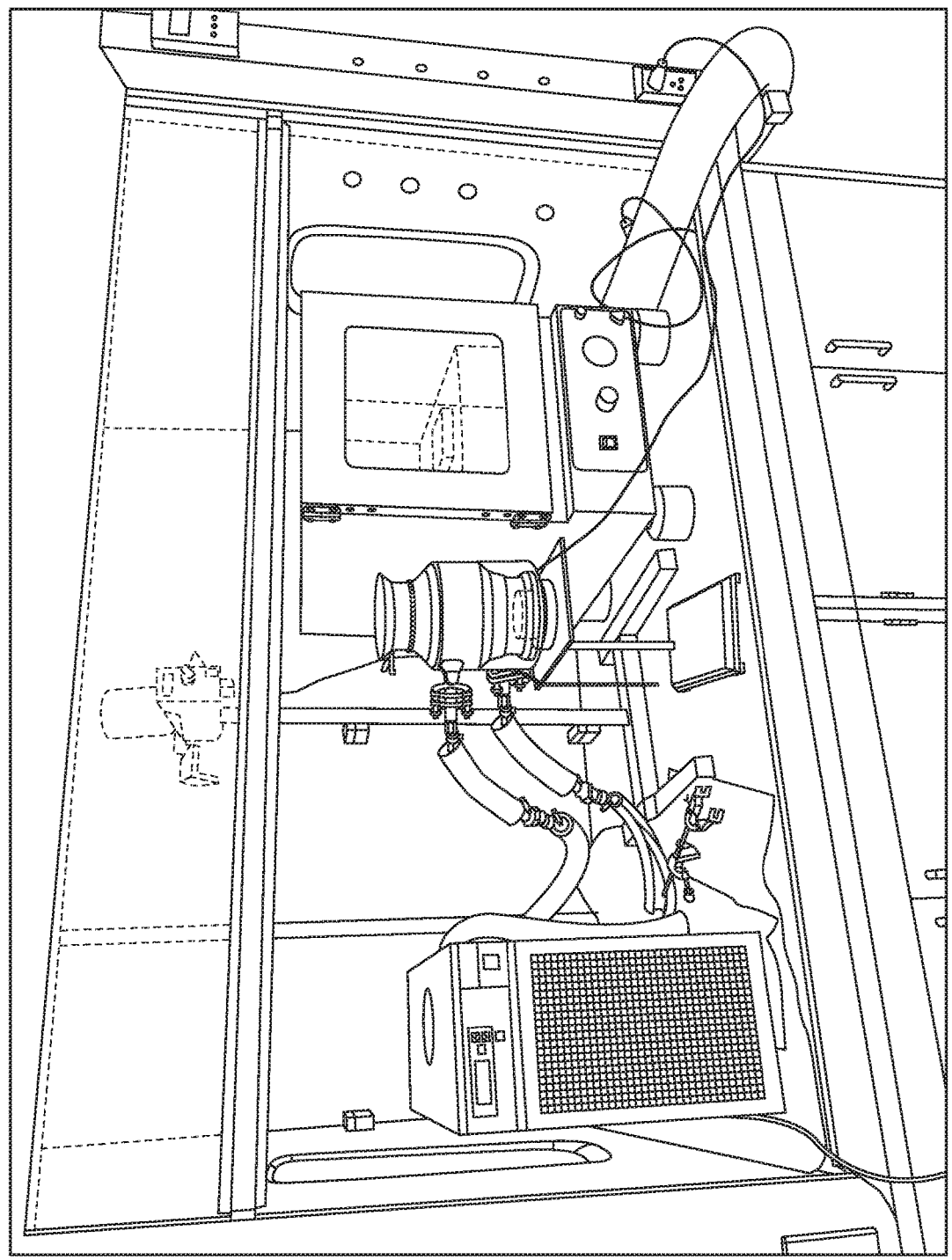
Figure 2C:
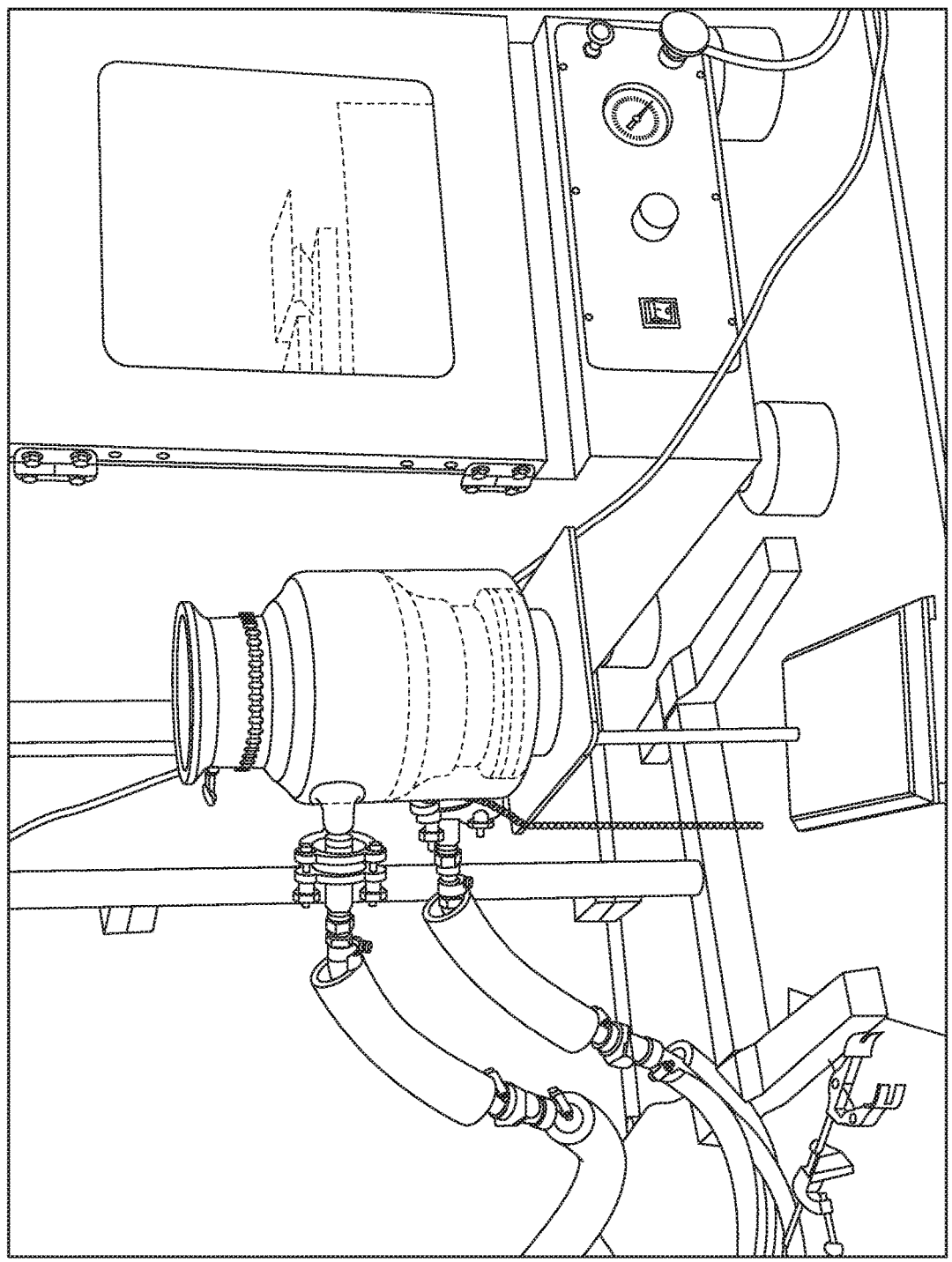
Figure 2D:
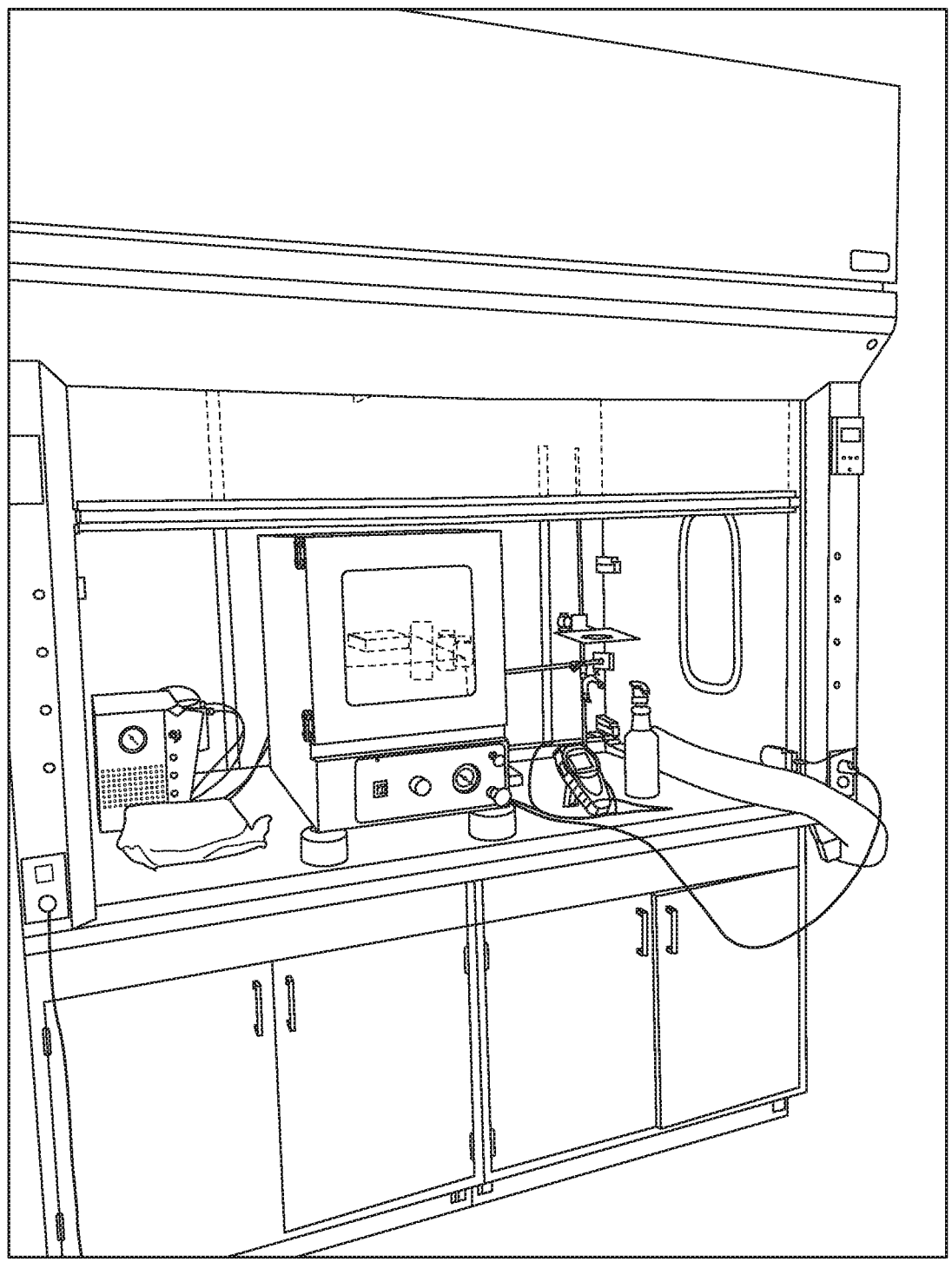
Figure 3:
FIG. 3 illustrates and example packaging for use with a product/supplement according to the disclosure.

This disclosure details, for the first time, purified cannabinoids added back to whole hemp extract to provide a dietary supplement. In particular, it is the first time that CBN has been used in a dietary supplement. This disclosure maintains the synergistic entourage effect of a whole-plant *Cannabis* extract (Russo 2011), while also allowing individual cannabinoids and/or ratios to be selected by and/or tailored for a consumer and/or particular indication. FIG. 1 provides a high-level overview of some methods of the disclosure, comprising: extracting cannabinoids from plant materials 1003 (such as one or more hemp varieties of *Cannabis sativa*), separating and purifying CBD from the extracted cannabinoids 1005; converting purified CBD to Δ9-THC and Δ8-THC and concurrently (and/or substantially concurrently) converting Δ9-THC to CBN 1007; purifying and separating the CBN and/or other cannabinoids 1009; and combining the purified CBN with a whole-plant extract 1011, such as a whole-plant extract of one or more hemp varieties of *Cannabis sativa*.

I. Purification of CBD

In one embodiment, CBD is crystallized from high CBD *Cannabis* extract, e.g., produced with a Waters supercritical $CO_2$ extractor (SFE) with fraction collectors, collected from either the first fraction collector, or in some embodiments the second fraction collector. Concentrated cannabinoids and other phytochemicals from the SFE can be added to non-polar organic solvent, such as at ratios of 1:3 to 1:5 w:w. Gentle heating in a water bath at 40° C. to 60° C. can be used to fully dissolve the concentrate. The resulting solution is slowly cooled to −8° C. to −10° C. over the course of 8 to 12 hours with constant agitation. Filtering the resulting mixture yields yellow to white crystals. This crystalline precipitate can then be recrystallized using the same procedure to obtain >99% pure CBD. CBD crystals are fine and white.

For example, in a particular implementation according to one embodiment, a solution of hemp concentrate dissolved in 99% n-heptane 1:3 w:w was held in jacketed a 2 L reactor with an anchor-blade PTFE agitator set to 80 rpm. Over the course of 2 hours, the reactor was chilled from ambient temperature to 0° C. After 1 hour of agitation, the reactor was chilled to −8° C. over the course of 4 hours. The solution was then agitated for 3 hours. The mother liquor was filtered off with Grade 5 Whatman filter paper.

The resulting crystals were yellowish white in colour. Purity is generally dependent on the wax content of the starting material, and typically ranges from 80-98% CBD w/w. Recrystallization using the above technique yielded purified (>99% w/w) CBD crystals. Heptane was dried off to <5000 ppm with no further processing. Impurities can vary based on a number of factors.

In some embodiment, the disclosed purification process can be used to crystallize other cannabinoids, including, by way of non-limiting example, (−)-trans-$Δ^9$-Tetrahydrocannabinolic acid (THCA-A) and cannabigerol (CBG).

II. Conversion of CBD to Δ9-THC, Δ8-THC, and Concurrent Conversion of Δ9-THC to CBN In one embodiment, purified CBD is held in an oven or heat chamber at one or more elevated (relative to room temperature) specified temperature(s) for a specified period of time, such as at 100° C. to 180° C. (and/or including any integers or ranges there between, including but not limited to from about 110° C. to about 170° C., from about 140° C. to about 160° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., etc.) for 24 to 168 hours (and/or including any integers or ranges there between). In some embodiments, at constant airflow at atmospheric pressure, while other embodiments at periodic or minimal airflow at reduced or raised pressure relative to atmospheric pressure.

In an example of a particular implementation of an embodiment, >99% CBD w/w crystals were spread in a thin layer across a pyrex dish in a solvent-safe vacuum oven. The oven was set to 165° C. and a vacuum pump was set to full vacuum while the oven vent was left fully open to exchange atmospheric air with the air inside the oven and provide atmospheric $O_2$ for the oxidation of Δ9-THC to CBN. The solid material was maintained at 165° C. for 168 hours with periodic opening of the oven door. HPLC analysis showed that the CBD initially converted to Δ9-THC and Δ8-THC. Δ9-THC simultaneously oxidized to CBN as it was exposed to heat. The resulting material was dark red/brown, glassy in appearance and texture, and composed of 3-20% CBN w/w, 3-12.5% Δ9-THC w/w, <10% Δ8-THC, and 50-90% w/w uncharacterized impurities based on HPLC, $^1$H-NMR, and QTOF LC/MS analysis.

In one embodiment, purified CBD is dissolved in an organic solvent phase, or in some embodiments an aqueous weak acid phase, at 1 mg/mL to 200 mg/mL. Then 1 to 1000 molar equivalents of 0.1 N to 1 N sulfuric acid ($H_2SO_4$) or 0.1 N to 1 N hydrochloric acid (HCL). Samples can be agitated to ensure homogeneity, then in some embodiments they are placed in a hot block at temperatures from 30° C. to 120° C. In some embodiments, sulfur powder, iron oxide, hydrogen peroxide, and/or other oxidizing agent(s) can be added. Samples can be held in the hot block for 8 to 168 hours (and/or including any integers or ranges there between). Depending on the embodiment, 3% to 30% (w/w) conversion of CBD to CBN can be achieved.

For example, in an implementation of one embodiment, a 100 mg/mL solution of 99% w/w CBD was prepared in a 6% v/v solution of ethanol and $H_2SO_4$. The reaction mixture was then heated to 120° C., and held at that temperature for 144 hours. A 10-11% w/w conversion to CBN was observed.

III. Purification of CBN and Other Cannabinoids by Supercritical Fluid Chromatography In one embodiment, enriched CBN material is dissolved in a nonpolar solvent, then injected onto a normal phase column held under isocratic mobile phase conditions. In some embodiments, the stationary phase is diol, bare silica, 2-ethyl pyridine, NH2, and/or the like. In some embodiments, the co-solvent mobile phase is a class III solvent such as, by way of non-limiting example, methanol, ethanol, ethyl acetate, isopropyl alcohol, and/or the like, ranging from 2% to 20% co-solvent. In some embodiments, the injection feed material solvent is a nonpolar solvent, such as, by way of non-limiting example, n-heptane, with up to 20% v/v of one of the previously mentioned polar co-solvents, whereas in some embodiments the injection solvent is 100% v/v class III polar solvent.

In an implementation of one embodiment, a 300 mg/mL feed solution of hemp extract in 99% n-heptane was used, under the conditions described in Table 1.

TABLE 1

Column conditions for analytical scale separation of cannabinoids.

| | |
|---|---|
| Column | Kromasil Diol 60 A, 4.6 × 250 mm, 10 μm, part no.: S10DIblk |
| Detection Wavelengths | 200-600 nm PDA |
| Column temperature | 40° C. |
| Pressure | 120 bar |

TABLE 1-continued

Column conditions for analytical scale separation of cannabinoids.

| | |
|---|---|
| Sample temperature | Ambient |
| Flow rate | 3 mL/min |
| Pump conditions | 90% $CO_2$, 10% Ethyl Acetate |
| Stop time | 30 mins |
| Injection volume | 250 μL |

In this embodiment, fractions collected from 8.5 to 12 minutes were >99% CBD by chromatographic peak area as determined by reverse-phase HPLC (Table 2).

In some embodiments, crystallization mother liquor can be used as a source of non-psychotropic cannabinoids such as cannabichromene (CBC), cannabidivarin (CBDV), and CBG for purification by SFC.

TABLE 2

Reverse-phase HPLC method conditions.

| | |
|---|---|
| Column | Restek Raptor ARC-18, 4.6 × 150 mm, 2.7 μm, Cat No: 9314A65 |
| Detection Wavelength | 220 nm |
| Column Temperature | 50° C. ± 2.0° C. |
| Sample Temperature | Ambient |
| Flow Rate | 1.5 mL/min |
| Injection Volume | 2 μL |
| Peakwidth | >0.05 min |
| Data Acquisition Time | 9 min |
| Stop Time | 9 min |

Pump Conditions: Mobile Phase A: 0.1% (v/v) formic acid in $H_2O$ B: 0.1% (v/v) formic acid in ACN

| Time (min) | Mobile Phase B (%) |
|---|---|
| 0.00 | 50 |
| 6.00 | 100 |
| 7.00 | 100 |
| 7.01 | 50 |
| 8.00 | 50 |
| 9.00 | 50 |

IV. Preparation of Dietary Supplement With Purified Cannabinoids

In some embodiments, purified CBD, CBC, CBG, CBN, CBDV or some combination thereof are added back into whole hemp extract to produce whole-plant extract dietary supplements with unique cannabinoid profiles not naturally found in *Cannabis* plant material.

For example, in an example implementation of one embodiment, purified CBD is mixed with whole hemp extract with a ratio of 20:1 to 50:1 CBD:Δ9-THC w:w in order to achieve a ratio of 200:1 final product. For example, one gram hemp concentrate with 600 mg/g CBD and 20 mg/g THC may be added to 3400 g of purified CBD to achieve a 200:1 ratio while retaining the less abundant secondary compounds found in the whole hemp concentrate. In some embodiments, this material can be diluted in a carrier oil to 50 mg/g CBD and 0.25 mg/g THC. The potential for a pschyotropic effect is thus greatly reduced.

In some embodiments, purified CBN can be dissolved in hemp concentrate and dissolved in a carrier oil to produce a finished product with a 1:1 ratio of CBN to CBD. For example, 600 mg of CBN can be dissolved 1 g of 600 mg/g CBD hemp concentrate with gentle heating. The resulting mixture can be dissolved in a carrier oil to produce 10 mg/g CBD and CBN product.

V. Conclusion

While various embodiments of the disclosure have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the disclosure. More generally, it should be appreciated and understood that all parameters, dimensions, materials, and configurations described herein are meant to be exemplary and that the actual parameters, dimensions, materials, and/or configurations can depend upon the specific application or applications for which the disclosed teachings is/are used. Those skilled in the art will recognize, or be able to ascertain using no more than routine experimentation, many equivalents to the specific disclosed embodiments described herein. It is, therefore, to be understood that the foregoing embodiments are presented by way of example only and that, within the scope of the appended claims and equivalents thereto; disclosed embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments can be implemented in any of numerous ways. For example, the embodiments (e.g., extraction, isolation, purification, and conversion of various cannabinoids, and modifications of whole-plant *Cannabis sativa* extracts therewith) may be implemented using a wide variety of methods, equipment, machinery, and/or a combination thereof.

Also, various disclosed concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

A flow diagram is used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedia components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

The indefinite articles "a" and "an," as used herein in the specification and in the claims, unless clearly indicated to the contrary, should be understood to mean "at least one."

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

The invention claimed is:

1. A method for preparing a *cannabis* extract enriched in cannabinol, said method comprising:
    (a) providing purified cannabidiol;
    (b) converting the purified cannabidiol to delta 9 tetrahydrocannabinol and delta 8 tetrahydrocannabinol, and concurrently converting the delta 9 tetrahydrocannabinol to cannabinol by heating the purified cannabidiol at 100° C. to 180° C. for at least 24 hours, thereby producing cannabinol; and
    (c) combining the cannabinol produced from step (b) with a *cannabis* extract, thereby producing the *cannabis* extract enriched in cannabinol.

2. The method of claim 1, wherein the *cannabis* extract enriched in cannabinol also comprises a cannabinoid selected from the group consisting of cannabidiol, cannabichromene, cannabigerol and cannabidivarin.

3. The method of claim 1, wherein the *cannabis* extract enriched in cannabinol also comprises cannabidiol.

4. The method of claim 1, wherein the *cannabis* extract is from one or more hemp varieties of *Cannabis sativa*.

5. The method of claim 1, wherein the purified cannabidiol is greater than 99% w/w cannabidiol.

6. The method of claim 1, wherein the purified cannabidiol comprises cannabidiol crystals.

7. The method of claim 3, wherein the *cannabis* extract enriched in cannabinol has a cannabinol:cannabidiol w:w ratio between 20:1 to 1:20.

8. The method of claim 3, wherein the *cannabis* extract enriched in cannabinol has a cannabinol:cannabidiol w:w ratio between 2:1 to 1:2.

9. The method of claim 3, wherein the *cannabis* extract enriched in cannabinol has a cannabinol:cannabidiol w:w ratio of 1:1.

10. The method of claim 1, wherein the *cannabis* extract enriched in cannabinol comprises delta 9 tetrahydrocannabinol.

11. The method of claim 10, wherein the *cannabis* extract enriched in cannabinol comprises cannabidiol and has a cannabidiol:delta 9 tetrahydrocannabinol w:w ratio between 20:1 to 500:1.

12. The method of claim 10, wherein the *cannabis* extract enriched in cannabinol comprises less than 1% by weight of delta 9 tetrahydrocannabinol.

13. The method of claim 10, wherein the *cannabis* extract enriched in cannabinol comprises less than 0.5% by weight of delta 9 tetrahydrocannabinol.

14. The method of claim 10, wherein the *cannabis* extract enriched in cannabinol comprises less than 0.3% by weight of delta 9 tetrahydrocannabinol.

15. The method of claim 1, wherein the purified cannabidiol that is converted in step (b) is not dissolved in an acid.

16. The method of claim 15, wherein the *cannabis* extract enriched in cannabinol also comprises cannabidiol.

17. The method of claim 16, wherein the *cannabis* extract enriched in cannabinol has a cannabinol:cannabidiol w:w ratio between 20:1 to 1:20.

18. The method of claim 16, wherein the *cannabis* extract enriched in cannabinol has a cannabinol:cannabidiol w:w ratio between 2:1 to 1:2.

* * * * *